US009060827B2

(12) United States Patent
Anitua Aldecoa

(10) Patent No.: US 9,060,827 B2
(45) Date of Patent: Jun. 23, 2015

(54) TOOL FOR DRILLING BONE TISSUE, PARTICULARLY SUITABLE FOR PERFORMING A SINUS LIFT ACCORDING TO THE SUMMERS TECHNIQUE OR FOR THE FITTING OF EXTRA-SHORT IMPLANTS

(75) Inventor: Eduardo Anitua Aldecoa, Vitoria (ES)

(73) Assignee: BIOTECHNOLOGY INSTITUTE, I MAS D, S.L., Vitoria (Alava) (ES)

( * ) Notice: Subject to any disclaimer, the term of this patent is extended or adjusted under 35 U.S.C. 154(b) by 47 days.

(21) Appl. No.: 13/238,574

(22) Filed: Sep. 21, 2011

(65) Prior Publication Data

US 2012/0078257 A1     Mar. 29, 2012

(30) Foreign Application Priority Data

Sep. 24, 2010   (ES) .................................. 201001225

(51) Int. Cl.
  *A61B 17/16*      (2006.01)
  *A61C 8/00*       (2006.01)

(52) U.S. Cl.
  CPC .............. *A61C 8/0089* (2013.01); *A61B 17/16* (2013.01); *A61B 17/1615* (2013.01); *A61B 17/1633* (2013.01); *A61B 17/1688* (2013.01); *A61C 8/0092* (2013.01)

(58) Field of Classification Search
  CPC .............. A61B 17/16; A61B 17/1604; A61B 17/1615; A61B 17/1617; A61B 17/162; A61B 17/1622; A61B 17/1631; A61B 17/1633; A61B 17/1635; A61B 17/1637; A61B 17/164; A61B 17/1662; A61B 17/1673; A61B 17/1688; A61B 17/32; A61B 17/320016; A61B 17/32002; A61B 2017/1602; B23B 51/0009; B23B 51/0018; B23B 51/0063; B23B 51/009; B23B 51/02; A61C 3/00; A61C 3/02; A61C 8/0092
  USPC ......... 606/79, 80, 180; 83/835, 849; 433/165, 433/166
  See application file for complete search history.

(56) References Cited

U.S. PATENT DOCUMENTS

| | | | | |
|---|---|---|---|---|
| 4,285,618 A | * | 8/1981 | Shanley, Jr. | 407/54 |
| 5,429,504 A | * | 7/1995 | Peltier et al. | 433/165 |
| 5,908,423 A | * | 6/1999 | Kashuba et al. | 606/80 |
| 6,238,398 B1 | * | 5/2001 | Lechot | 606/80 |
| 6,319,005 B1 | * | 11/2001 | Hollander et al. | 433/165 |
| 6,402,438 B1 | * | 6/2002 | Boyer | 408/144 |
| 2005/0283160 A1 | * | 12/2005 | Knisely et al. | 606/80 |
| 2010/0196844 A1 | * | 8/2010 | Heo | 433/114 |

* cited by examiner

*Primary Examiner* — Michael T Schaper
*Assistant Examiner* — Tracy Kamikawa
(74) *Attorney, Agent, or Firm* — Browdy and Neimark, PLLC

(57) ABSTRACT

A tool for drilling bone tissue, which has the advantage of having a cutting tip with a flat effective shape that prevents perforation of the Schneider membrane or injury to the dental nerve when drilling close to them. The tool is disposed along an longitudinal axis and includes a non-cutting main body, a narrowed area for retaining bone and a cutting tip, which includes cutting blades, each one of which is provided with a front cutting edge substantially perpendicular to the longitudinal axis and a substantially lateral cutting edge that forms an angle of between 0 and 10° with the longitudinal axis. Spaces for receiving bone are disposed between the cutting blades and are connected to the narrowed area.

4 Claims, 3 Drawing Sheets

TOOL FOR DRILLING BONE TISSUE, PARTICULARLY SUITABLE FOR PERFORMING A SINUS LIFT ACCORDING TO THE SUMMERS TECHNIQUE OR FOR THE FITTING OF EXTRA-SHORT IMPLANTS

TECHNICAL FIELD

The invention relates to a tool for drilling bone tissue, particularly (but not exclusively) suitable for performing a sinus lift according to the Summers technique. Another application for which the tool may be useful is for the fitting of extra-short implants (of a length shorter than or equal to 7.5 mm).

PRIOR ART

Jawbones are provided with internal bone cavities called maxillary sinuses. Along with the nasal cavities, these cavities are situated in the central area of the craniofacial complex and apparently perform different functions such as lightening the weight of the jawbone, moistening and warming air, and acting as an intracranial mechanical insulator in the event of a traumatism. The walls of the maxillary sinuses are covered by a fine layer of mucus known as the Schneider membrane, the functions of which are to heat inhaled air and generate a secretion that moistens the inhaled air and that retains the solid particles it may contain. Said membrane can easily be removed from the walls without causing a hemorrhage.

The bone situated beneath the maxillary sinuses, commonly known as the subantral maxillary segment, is a potential dental-implant receptor site. The fitting of an implant in said subantral maxillary segment may be hampered to a greater or lesser extent, as is the case with any bone where an implant is to be fitted, due to the general condition of the bone and its dimensions. For example, a circumstance that frequently arises is that the subantral maxillary segment is very thin and is not able to host a dental implant suitably, as the implant would not have sufficient bone tissue around it to osseointegrate correctly and would perhaps invade the maxillary sinus and even deteriorate the Schneider membrane. To address this problem a surgical procedure known as sinus lift is carried out, which allows increasing the thickness of the subantral maxillary segment (thus reducing the height of the maxillary sinus).

The sinus lift procedure may be performed according to various techniques. One of the most widely used is the alveolar approach or Summers technique. In the Summers technique it is first of all necessary to ascertain the height of the subantral maxillary segment. Then, firstly and with the help of osteotomes or drills, a bone cavity or alveolus is prepared in the subantral maxillary segment until almost the very end of it is reached (in other words, until the Schneider membrane and the maxillary sinus is almost reached), but without passing through it completely, so that there is no risk that the osteotomes and, especially, the drills perforate the membrane. Then, when there is only a thin layer of bone left to drill, generally 1 or 2 mm thick, osteotomes or drills of a greater diameter are successively used, on the tip of which bone tissue particles produced as a result of the drilling are accumulated. Said accumulation gradually causes the lifting of the Schneider membrane, beneath which the space is filled with particles of bone tissue. Optionally, prior to the use of the osteotomes or drills of a greater diameter, bone graft may be inserted in the alveolus, which is then pushed by the osteotomes or drills to also contribute to filling the space beneath the raised Schneider membrane.

A slight variation of the Summers technique involves, once the alveolus has been drilled to within 1 or 2 mm before the end of the subantral maxillary segment, gently hammering with a tool to break the last portion of bone. Graft material is then inserted in the floor of the alveolus and beneath the Schneider membrane and pushed just enough to raise the membrane. Studies have been published describing the adverse secondary effects of this particular technique, some of which may be serious (dizziness, vertigo, etc.), especially related to the considerable trauma involved in the technique.

In the two techniques explained above, once the subantral maxillary segment has been drilled to within a depth of 1 or 2 mm of its total thickness and an additional tool (an osteotome or a piece that is able to be gently hammered) has been applied to break the last part of the bone, there is the risk of perforating the Schneider membrane, which may cause serious complications (sinusitis, etc.).

It is an objective of this invention to provide a new tool that is particularly suitable for performing a sinus lift according to the Summers technique, which enables the last part of the subantral maxillary segment to be broken without any risk to the Schneider membrane and without causing the adverse secondary effects known in some techniques.

BRIEF DESCRIPTION OF THE INVENTION

It is an object of this invention to provide a tool for drilling bone tissue, which has the advantage of having a cutting tip with a substantially-flat effective shape, to avoid perforating the Schneider membrane when drilling close to it during a sinus lift procedure according to the alveolar process or Summers technique. The tool is substantially disposed along a longitudinal axis in relation to which it may rotate. As main elements, the tool comprises a main body, a narrowed area to retain bone, and a cutting tip. The cutting tip comprises a series of cutting blades, each one of which is provided with a front cutting edge substantially perpendicular to the longitudinal axis and a lateral cutting edge substantially parallel to the longitudinal axis (specifically, forming an angle of between 0 and 10° with the longitudinal axis). Between the cutting blades there are spaces for receiving bone, which are in turn corrected to the narrowed area.

As a result, when the tool rotates, the cutting tip of the tool acquires a substantially flat shape (perpendicular to the longitudinal axis, i.e., not pointed). This allows that the last portion of subantral maxillary segment, in the proximity of the Schneider membrane, may be drilled without the risk of the drill perforating the membrane (as a result of which it is preferable that the approach is gentle). In addition, the particles of bone tissue produced during the drilling are removed from the cutting tip towards the narrowed area of the tool, preventing them from exerting additional pressure on the Schneider membrane.

As explained above, the inventive tool for drilling bone tissue is particularly suitable for use when performing a sinus lift according to the Summers technique. However, it is also very useful for other uses, such as assisting with the fitting of extra-short implants (of a length shorter than or equal to 7.5 mm); in this case, the inventive tool allows implants with a small apex to be fitted and thereby enables the whole length of the implant to be used, thanks to the fact that the tool has a flat end rather than a pointed end and that it therefore drills a substantially cylindrical alveolus that may be wholly occupied by the implant.

BRIEF DESCRIPTION OF THE DRAWINGS

Details of the invention can be seen in the accompanying non-limiting drawings.

DETAILED DESCRIPTION OF THE INVENTION

The drawings accompanying this description show three views of the preferred embodiment of the inventive tool.

Figure 1:
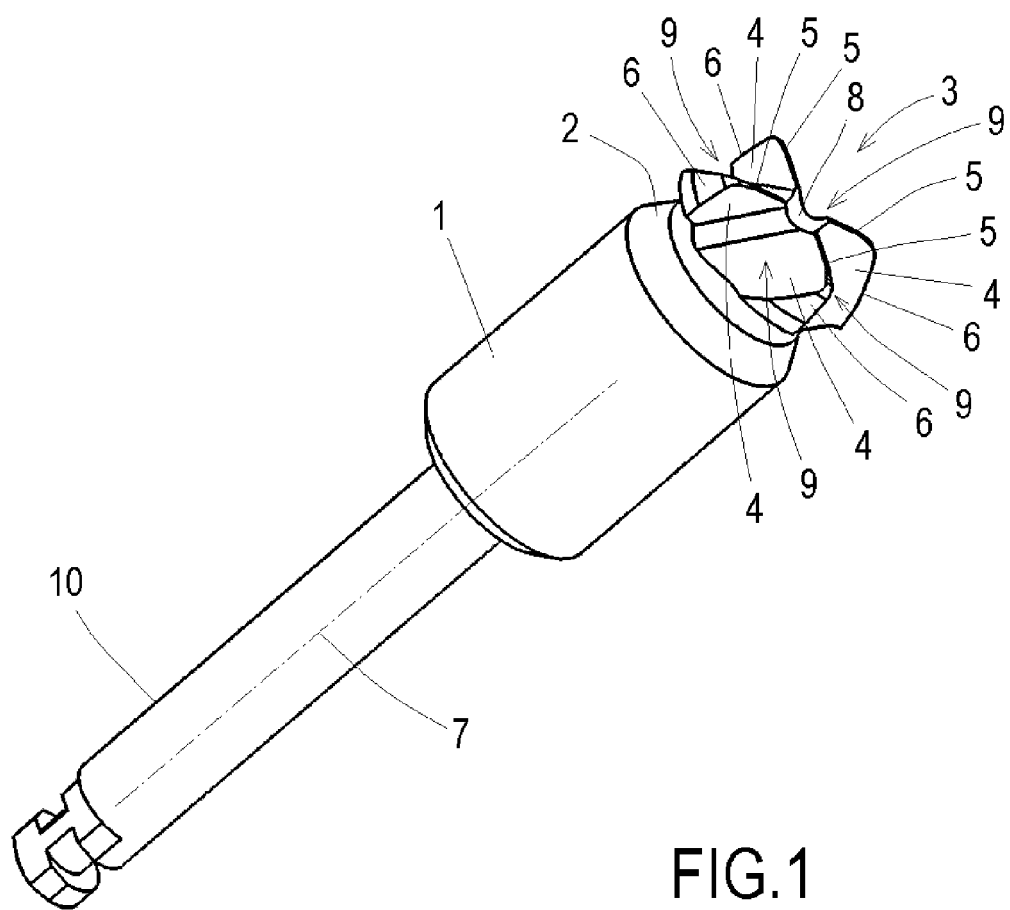
FIG. 1 shows a perspective of the preferred embodiment of the tool according to the invention.

As can be seen in FIG. 1, which shows a perspective of the preferred embodiment of the tool, the tool comprises a non-cutting main body (1), a narrowed area (2) and a cutting tip (3). The cutting tip (3) also comprises a series of cutting blades (4), each one of which is provided with a front cutting edge (5) substantially perpendicular to the longitudinal axis (7) in relation to which the tool is disposed and in relation to which said tool is designed to rotate. The cutting tip (3) also comprises a lateral cutting edge (6) substantially parallel to the longitudinal axis (7), more specifically forming an angle of between 0 and 10° with said longitudinal axis (7). The narrowed area (2) acts as an area for collecting bone. In addition, spaces (9) for receiving bone are disposed between the cutting blades (4) and connected to the narrowed area (2), preventing the blunting of the tool due to the bone debris, as explained below.

When the drilling tool is rotating, the effective cutting tip (3) is approximately rectangular, in other words it is substantially flat due to the fact that the front cutting edges (5) are substantially perpendicular to the longitudinal axis (7). This allows the tool to cut the bone in an extremely controlled manner, without the tool presenting a pointed apex that may perforate the Schneider membrane undesirably (or, in the case of its use for drilling the jawbone for the purpose of fitting an extra-short implant, prevents the tool from injuring the dental nerve). This advantage is enhanced by the fact that the bone particles produced as a result of the drilling are accumulated in the spaces (9) for receiving bone situated between the cutting blades (4), and removed towards the narrowed area (2) for retaining bone, preventing the accumulation of bone particles in the tip of the tool, which could cause the shaft tip to stop having a rectangular effective shape.

In practice it has been shown that, given that the Schneider membrane is elastic, the rectangular effective cutting tip (3) not only does not cut the membrane but is also capable of pushing and moving the membrane without breaking it, provided that the approach with the tool is performed in a controlled manner. In other words, the tool according to the invention contributes to correctly perform a sinus lift according to the Summers technique, not only by not drilling the Schneider membrane but by moving it was well. In order to help perform the technique, the tool may be provided with some depth marks.

In addition, as can be seen, the main body (1) is substantially cylindrical, so that said main body (1) can act as a guide during the advance of the tool inside the alveolus, while not enlarging the alveolus.

Figure 2:
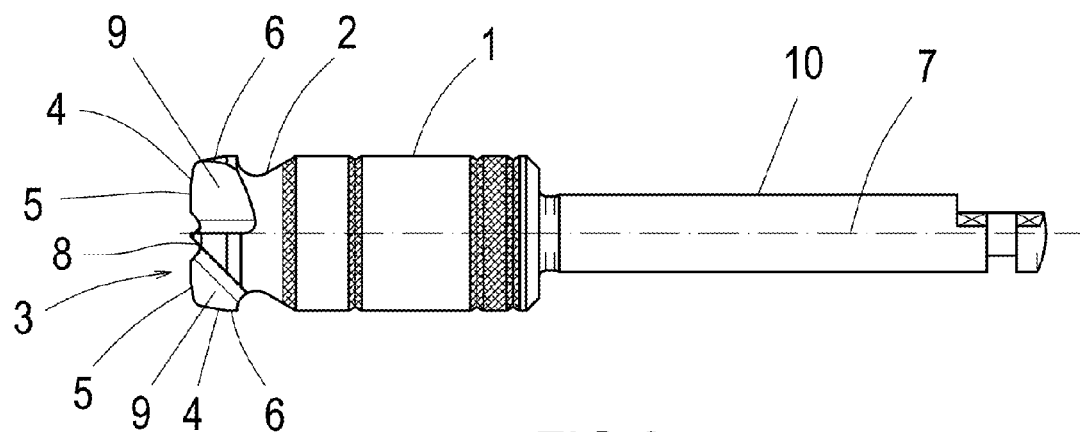
FIG. 2 shows a front view of the tool of the previous figure.

As can be seen in FIG. 2, which shows a front view of the tool, the narrowed area (2) is substantially conical in shape. The conical shape allows the procedure for manufacturing the piece to be simplified and makes the piece easier to clean.

FIG. 2 also shows that the lateral cutting edge (6), substantially parallel to the longitudinal axis (7), forms in one embodiment a slight angle in relation to said longitudinal axis (7). Said angle is comprised between 1 and 10°, helping center the tool during its insertion in the alveolus. Said angle also enables the advance to be controlled, as the bone that is perforated is approximately conical in shape and of a reduced size, and the slightly conical shape of the tool therefore allows a reduction in the risk of the bone being perforated incorrectly.

Figure 3:
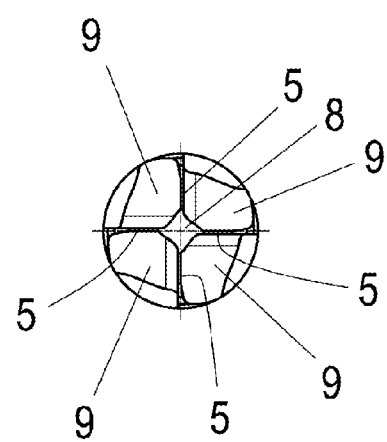
FIG. 3 shows a side view of the tool of FIG. 2.

Additionally, as can be seen in the three figures and in particular in FIG. 3, which shows a side view of the tool, the front cutting edges (5) of the cutting blades (4) are disposed around a central recess (8). Said central recess (8) is capable of storing a certain amount of bone particles produced as a result of the drilling, which ensures, in the event of unwanted bone particles accumulating in the area of the cutting tip during drilling, that these particles do not accumulate to form a point that becomes a cutting edge, which might break the Schneider membrane.

Figure 4:
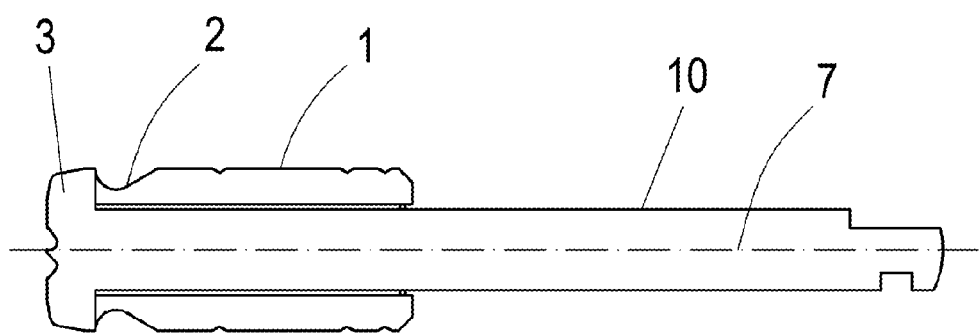
FIG. 4 shows a cross-sectional front view of another embodiment of the tool according to the invention.

FIG. 4 shows a second embodiment of the tool according to the invention, the tool being shown in cross-section. As shown, in this embodiment the shaft (10) and the cutting tip (3) are connected to each other and may rotate in relation to the main body (1). This allows the tool to be used in two phases. In a first phase the tool is inserted in the alveolus, with the main body (1) being made to slide all the way along the walls of the alveolus, without the need to rotate the tool, thus making the guiding and control of the advance easier and more precise. In a second phase, when the tool has already been inserted to the necessary depth, the tool is operated to cause the rotation of the shaft (10) and the cutting tip (3), initiating the drilling, without this causing the rotation of the main body (1), thereby preventing additional and unnecessary drilling and wear of the alveolus.

The invention claimed is:

1. A tool for drilling bone tissue, substantially arranged along a longitudinal axis in relation to which said tool is designed to rotate, comprising:
   a shaft, a cylindrical non-cutting main body, a narrowed area and a cutting tip;
   wherein,
      the cutting tip comprises a series of cutting blades, each one of which comprises a straight front cutting edge substantially perpendicular to the longitudinal axis and a straight lateral cutting edge that forms an angle of from 1 to 10° along its entire length with the longitudinal axis,
   where said narrowed area is located right between the main body and the straight lateral cutting edges of the series of cutting blades, is radially narrower than the main body and the cutting tip, and is devoid of cylindrical outer surfaces, providing a bone-particle-retaining area that retains bone particles during use of the tool; and
   wherein bone-particle-retaining spaces are disposed between adjacent ones of the series of cutting blades and are communicated with the narrowed area.

2. The tool according to claim 1, wherein the narrowed area is substantially conical.

3. The tool according to claim 1, wherein the straight front cutting edges of the series of cutting blades are disposed around a central recess.

4. The tool according to claim 1, wherein the shaft and the cutting tip are connected to each other and may rotate in relation to the main body.

* * * * *